(12) United States Patent
Ikeda et al.

(10) Patent No.: US 7,651,706 B2
(45) Date of Patent: Jan. 26, 2010

(54) LIQUID PREPARATION CONTAINING CRUDE-DRUG EXTRACT

(75) Inventors: Yoichi Ikeda, Hiroshima (JP); Mizuho Ono, Hiroshima (JP); Katsunori Nishimura, Hiroshima (JP)

(73) Assignee: Wakunaga Pharmaceutical Co., Ltd., Osaka-shi (JP)

( * ) Notice: Subject to any disclaimer, the term of this patent is extended or adjusted under 35 U.S.C. 154(b) by 623 days.

(21) Appl. No.: 10/488,924

(22) PCT Filed: Sep. 12, 2002

(86) PCT No.: PCT/JP02/09333

§ 371 (c)(1),
(2), (4) Date: Mar. 12, 2004

(87) PCT Pub. No.: WO03/024466

PCT Pub. Date: Mar. 27, 2003

(65) Prior Publication Data

US 2004/0241253 A1 Dec. 2, 2004

(30) Foreign Application Priority Data

Sep. 13, 2001 (JP) .............................. 2001-277673

(51) Int. Cl.
*A61K 36/8962* (2006.01)
*A61K 36/00* (2006.01)

(52) U.S. Cl. ....................... 424/754; 424/725

(58) Field of Classification Search ........................ None
See application file for complete search history.

(56) References Cited

U.S. PATENT DOCUMENTS

| 2,618,561 | A | * | 11/1952 | Spinka et al. ................ 424/754 |
| 5,260,090 | A | * | 11/1993 | Isao ........................... 426/638 |
| 5,401,526 | A | * | 3/1995 | Tomita ........................ 426/615 |
| 5,453,420 | A | * | 9/1995 | Sakai .......................... 514/12 |
| 6,146,638 | A | * | 11/2000 | Kakimoto et al. ....... 424/195.15 |

FOREIGN PATENT DOCUMENTS

| JP | 56082076 | * | 7/1981 |
| JP | 61-268627 | | 11/1986 |
| JP | 09163973 | * | 6/1997 |
| JP | 9-227394 | | 9/1997 |
| JP | 11-130681 | | 5/1999 |
| JP | 11-171793 | | 6/1999 |
| JP | 2000-38345 | | 2/2000 |
| JP | 2000-169385 | | 6/2000 |
| JP | 2000-247890 | | 9/2000 |
| JP | 2000-290186 | * | 10/2000 |
| JP | 2001-131070 | | 5/2001 |
| JP | 2001-158747 | | 6/2001 |
| JP | 2001-288101 | | 10/2001 |
| JP | 2001299261 | * | 10/2001 |
| JP | 2003-81846 | | 3/2003 |
| KR | 9008827 | * | 11/1990 |
| KR | 9105285 | * | 7/1991 |
| KR | 9302180 | * | 3/1993 |
| KR | 2001044329 | * | 6/2001 |
| RU | 2000065 | * | 9/1993 |

OTHER PUBLICATIONS

Machine Translation from Japanese Patent Office website provided for JP 2000-290186, published Oct. 17, 2000.*
Matsuura, H., Saponins in garlic as modifiers of the risk of cardiovascular disease, Mar. 2001, The Journal of Nutrition, 131(3s):1000S-5S.*
Saccharides. Dictionary.com. [online] The American Heritage® Dictionary of the English Language, Fourth Edition. Houghton Mifflin Company, 2004. Retrieved from http://dictionary.reference.com/browse/saccharides [Retrieved on Mar. 29, 2007].*
Sugar Alcohols Fact Sheet, International Food Information Council website [Online], retrieved fromhttp://ific.org/publications/factsheets/sugaralcoholfs.cfm [Retrieved on Mar. 29, 2007].*

* cited by examiner

*Primary Examiner*—Christopher R. Tate
(74) *Attorney, Agent, or Firm*—Oblon, Spivak, McClelland, Maier & Neustadt, L.L.P.

(57) ABSTRACT

The present invention relates to a liquid preparation containing crude drug extracts in an amount of 5 to 50 w/v % in terms of a dry extract weight based on the whole amount of the liquid preparation, characterized by containing saccharides in an amount of 5 to 40 w/v % based on the whole amount of the liquid preparation and adjusting a pH to 4.5 to 5.5.

This liquid preparation is suppressed in generating precipitate and suspended content with the course of time even if the crude drug extracts are contained in a high concentration and which is stable over a long period of time.

9 Claims, No Drawings

LIQUID PREPARATION CONTAINING CRUDE-DRUG EXTRACT

FIELD OF INVENTION

The present invention relates to a liquid preparation containing crude drug extracts which is suppressed in generating a precipitate and a suspended contents with the course of time and which is stable over a long period of time.

BACKGROUND OF THE INVENTION

Crude drugs are used as an active ingredient for cold and stomach medicines, nourishing tonics and the like. Many oral liquid preparations containing crude drug extracts are sold for practical use. A dosage of these commercially available liquid preparations containing crude drug extracts are usually 25 to 100 mL. However, considering the compliance of the consumers, who are old persons, children and persons having a weaker physical strength due to diseases, a dosage of medicines should preferably be reduced as much as possible. In order to administer a minimum dose, and furthermore to be effective even in a reduced dosage, crude drug extracts have to be contained in the whole amount of a liquid preparation in a high concentration. In this case, as a concentration of the crude drug components increases, contact between the crude drug components increases to cause aggregation, resulting in the problem that a generating amount of precipitate and turbidity increase with the course of time.

pH of a liquid preparation containing crude drug extracts has to be set up as low as possible to maintain the taste and the preservation. On the other hand, it is known that precipitation and turbidity are generated with the course of time by reducing the pH, and it has resulted in bringing about the problems that an unpleasant feeling is given to the consumers and the product value is damaged and that an influence to the effectiveness is concerned about.

In these liquid preparations containing crude drug extracts, generally it is well known that surfactants used as a solubilizer suppress the generation of precipitation and turbidity with the course of time. In this method, however, there have been the problems that a large amount of surfactants is required and therefore an influence exerted to organisms by the surfactants is concerned about and that the surfactants are susceptible to hydrolysis at a lower pH and therefore the solubilizing effect is reduced.

A method for preventing precipitation and turbidity originating in a crude drug by adding a polyoxyethylene-hardened castor oil derivative and polyvinylpyrrolidone at pH 3.0 to 4.5 is reported in Japanese Patent Application Laid-Open No. 61-268267, and a liquid preparation containing crude drug extracts which is adjusted to have a pH of 2.2 to 3.8 by adding polyoxyethylene-polyoxypropylene glycol and which is stable over a long period of time is reported in Japanese Patent Application Laid-Open No. 2000-38345. However, these methods are not sufficient, and it is difficult to apply them to liquid preparations containing crude drug extracts in a high concentration.

Accordingly, an object of the present invention is to provide a stable liquid preparation containing crude drug extracts which is suppressed in generating precipitate and suspended contents with the course of time even if crude drug extracts are contained in a high concentration.

SUMMARY OF THE INVENTION

Investigations carried out by the present inventors in order to solve such problems as described above have resulted in finding that in a liquid preparation containing crude drug extracts in an amount of 5 to 50 w/v % in terms of a dry weight amount based on the whole amount of the liquid preparation, precipitation and turbidity generated with the course of time can be suppressed by adding saccharides in an amount of 5 to 40 w/v % based on the whole amount of the liquid preparation and adjusting the pH to 4.5 to 5.5, and thus they have completed the present invention.

That is, the present invention provides a liquid preparation containing crude drug extracts in an amount of 5 to 50 w/v % in terms of a dry weight amount based on the whole amount of the liquid preparation, characterized by containing saccharides in an amount of 5 to 40 w/v % based on the whole amount of the liquid preparation and adjusting the pH to 4.5 to 5.5.

Further, the present invention provides a liquid preparation containing crude drug extracts in an amount of 5 to 50 w/v % in terms of a dry weight amount based on the whole amount of the liquid preparation which is suppressed in generating a precipitate originating in the crude drug, characterized by containing saccharides in an amount of 5 to 40 w/v % based on the whole amount of the liquid preparation and adjusting the pH to 4.5 to 5.5.

DETAILED DESCRIPTION OF THE INVENTION

In the present invention, a crude drug means the whole or a part of materials existing in nature such as plants, animals and minerals which can be used for medicines as they are or by processing. Examples include, for example, compounds described in official documents such as Japanese Pharmacopoeia or the other general purpose crude drugs, such as mallotus bark, gambir, aloe, epimedium grandiflorum morren, fennel, mume fructus, linderae radix, bearberry leaf, curcumae rhizoma, rose fruit, acanthopanax senticosus harms, corydalis tuber, plectranthi herba, astragalus root, scutellaria root, polygonati rhizoma, phellodendron bark, pruni jamasakura cortex, coptis rhizome, polygala root, phocae thstis et penis, hippocampus, polygoni multiflori radix, zedoary, pueraria root, japanese valerian, chamomillae flos, guarana, glycyrrhiza, platycodon root, immature orange, ox bile, apricot kernel, lycii fructus, schizonepeta spike, cinnamon bark, cassia seed, gentian, geranium herb, red ginseng, magnolia bark, oriental bezoar, acanthopanacis radicis cortex, achyranthes root, evodia fruit, schisandra fruit, bupleurum root, asiasarum root, thyme, salvia, smilax rhizome, crataegi fructus, gardenia fruit, cornus fruit, zanthoxylum fruit, zyzyphi semen, dioscorea rhizome, rehmannia root, civet, peony root, cnidii monnieris fructus, plantago herb, houttuynia herb, amomum seed, ginger, gardamon, ligustri fructus, lumbricus, magnoliae flos, senega, cnidium rhizome, peucedani radix, swertia herb, atractylodes lancea rhizome, mulberry bark, perilla herb, rhubarb, jujube, clove, uncariae uncis cum ramlus, citrus unshiu peel, capsicum, japanese angelica root, codonopsis pilosula nannf., cordyceps, peach kernel, bitter orange peel, ipecac, cuscutae semen, eucommiae cortex, nandinae fructus, gramineneae zea mays L, cistanchis herba, ginseng, garlic, ophiopogon tuber, glehnia root, pinellia tuber, agkistrodon, atractylodes rhizome, poria sclerotium, sinomenium stem, psoraleae semen, moutan bark, humulus lupulus L., ephedra herb, actinidiae fructi galla, muira puama, saussurea root, coix seed, longan arillus, japanese gentian, scopolia rhizome, and cornu cervi parvum. In addition thereto, it includes vegetal, mineral and animal crude drugs to which pharmacological effects can particularly be expected, such as chrysanthemi flos, wheat's shoot, safflower, salacia, blueberry, rosemary, lonicerae folium cum caulis, panax notoginseng F. H. chen, and ginkgo. The crude drug extract of the present invention includes extracts which are extracted from at least one of such crude drugs by a publicly known method. A method for extracting the respective crude drugs shall not specifically be restricted, and capable of being used are tinctures, fluidextracts, viscous extracts and dry extracts which are produced by publicly known methods, for example, methods shown in Japanese Pharmacopoeia.

Further, included as well in the crude drug extract of the present invention are extracts obtained from organs such as livers, hearts or placentas of animals and hydrolyzed products produced by processing these extracts with acids, bases or enzymes.

Among such crude drug extracts, preferably included is one or more crude drug extracts selected from animal and vegetal extracts comprising epimedium grandiflorum morren, oriental bezoar, civet, Cuscutae semen, garlic, ginseng, panax notoginseng F. H. chen, and cornu cervi parvum and hydrolyzed products of animal organs. One or more of crude drug extracts containing at least a garlic extract is particularly preferred.

In a certain case, solvents such as alcohol used in a certain case in extracting may remain in these crude drug extracts.

In the case of a tincture and a fluid extract, an amount of the dry weight extracts means an amount of solid content residue by evaporation, i.e., it can be lead from the residual weight (evaporation residue) obtained from 10 ml of a tincture or a fluid extract in a beaker whose weight is known, drying it up on a boiling water bath by evaporation, drying at 105° C. for 6 hours and then cooling in a desiccator (containing silica gel). For example, an amount of a solid content in 1 mL of a tincture having 300 mg of an evaporation residue is 30 mg. In the case of a viscous extract, an amount of the dry weight in the crude drug extracts means a solid content amount converted from a drying loss obtained by a test method prescribed in Japanese Pharmacopoeia. For example, an amount of a solid content contained in 1 g of a viscous extract having a loss on drying of 60% is 400 mg.

The saccharides used in the present invention include sugar alcohol, monosaccharides, disaccharides, polysaccharides and mixtures thereof. Sugar alcohol, monosaccharides and disaccharides are preferred, and sugar alcohol is particularly preferred. A blending amount of these saccharides can be used in the range of 5 to 40 w/v % based on the whole amount of the oral liquid preparation, and it is preferably 10 to 40 w/v %, more preferably 20 to 30 w/v %.

The sugar alcohol includes erythritol, xylitol, maltitol, mannitol, D-sorbitol, lactitol, glycerol, inositol and mixtures thereof and preferably includes sorbitol or xylitol, even more preferably xylitol.

The monosaccharides include fructose, fucose, mannose, glucose, galactose and ribose, and fructose, glucose and galactose are particularly preferred.

The disaccharides include sucrose, maltose, lactose and invert sugar, and sucrose and maltose are particularly preferred.

Oligosaccharide is preferred as the polysaccharides.

The liquid preparation containing the crude drug extracts of the present invention can be obtained, for example, by dissolving one or more of the crude drug extracts in water, centrifuging, if necessary, to remove insoluble matters, adding saccharides to the resulting aqueous solution and stirring, then suitably adding a pH controller to adjust the pH to 4.5 to 5.5, adding water to the whole amount and then filtrating.

In this respect, the pH controller includes acids such as citric acid, acetic acid, phthalic acid, succinic acid, maleic acid, aspartic acid, adipic acid, glutamic acid, fumaric acid, phosphoric acid, hydrochloric acid, nitric acid, sulfuric acid, tartaric acid and malic acid and bases such as potassium hydroxide, sodium hydroxide, calcium hydroxide, potassium hydrogencarbonate, sodium hydrogencarbonate, potassium carbonate, calcium hydrogencarbonate, sodium carbonate and calcium carbonate.

Capable of being added, if necessary, to the liquid preparation of the present invention are components usually used for oral liquid preparations, such as vitamins B1; thiamin, thiamin nitrate, thiamin hydrochloride, fursultiamine, bisbenthiamin, benfothiamin, thiamin disulfide, disethiamin, thiaminpropyl disulfide and derivatives thereof, vitamins B2; roboflavin and derivatives thereof and salts thereof, vitamins B3; niacin, nicotinic acid, nicotinic acid amide and derivatives thereof and salts thereof, vitamins B5; panthenol, pantothenic acid and derivatives thereof and salts thereof, vitamins B6; pyridoxine and derivatives thereof and salts thereof, vitamins B12; cyanocobalamine and derivatives thereof, the other vitamins; vitamin A, vitamin C, vitamin E, vitamin K, vitamin P and the like, sweeteners; glucose, fructose, reducing maltose, saccharin, single syrup, sucrose, aspartame, erythritol, sorbitol, mannitol, starch syrup and honey, preservatives; benzoic acid and salts thereof, ethyl paraoxybenzoate, propyl paraoxybenzoate and butyl paraoxybenzoate, amino acids; arginine, tryptophan, aspartic acid, lysine and taurine, dispersion aids; carboxymethyl cellulose, popidone and gum arabic, dissolution aids; ethanol, polyoxyethylene-hardened castor oil, glycerin fatty acid esters, decaglycerin fatty acid esters and polyglycerin fatty acid esters, colorants such as caramel and flavoring agents.

EXAMPLES

The liquid preparation of the present invention shall be explained below with reference to examples, but the present invention shall by no means be restricted by them.

In all examples and comparative examples shown below, the whole amount was set to 50 mL or 60 mL, and these solutions were filtered and then filled into test tubes. The test tubes were sealed with caps and used as test solutions.

Example 1

A ginseng viscous extract 4.67 g in terms of a dry weight was sufficiently stirred in a suitable amount of purified water, and xylitol 5.0 g was added thereto and dissolved. Then, 10% hydrochloric acid was used to adjust the pH to 5.0, and the whole amount was set to 50 ml with purified water (Sample 1).

Example 2

An epimedium grandiflorum morren viscous extract 3.38 g in terms of a dry weight was sufficiently stirred in a suitable amount of purified water, and xylitol 10.0 g was added thereto and dissolved. Then, sodium hydrogencarbonate was used to adjust the pH to 5.0, and the whole amount was set to 50 ml with purified water (Sample 2).

Example 3

A Cuscuta chinensis Lam. viscous extract 3.40 g in terms of a dry weight was sufficiently stirred in a suitable amount of purified water, and xylitol 10.0 g was added thereto and dissolved. Then, 10% hydrochloric acid was used to adjust the pH to 4.5, and the whole amount was set to 50 ml with purified water (Sample 3).

Example 4

A garlic viscous extract 14.1 g in terms of a dry wieght was sufficiently stirred in a suitable amount of purified water, and xylitol 15.0 g was added thereto and dissolved. Then, 10% hydrochloric acid was used to adjust the pH to 5.0, and the whole amount was set to 50 ml with purified water (Sample 4).

Example 5

A liver-hydrolyzed product viscous extract 2.50 g in terms of a dry weight was sufficiently stirred in a suitable amount of purified water, and xylitol 15.0 g was added thereto and dissolved. Then, 10% hydrochloric acid was used to adjust the pH to 4.5, and the whole amount was set to 50 ml with purified water (Sample 5).

Example 6

Oriental benzoar tincture 3.17 mg in terms of a dry substance, a civet tincture 4.10 mg in terms of a dry weight, a garlic viscous extract 14.1 g in terms of a dry weight and a ginseng viscous extract 4.67 g in terms of a dry weight were sufficiently stirred in a suitable amount of purified water, and xylitol 10.0 g was added thereto and dissolved. Then, 10% hydrochloric acid was used to adjust the pH to 5.0, and the whole amount was set to 50 ml with purified water (Sample 6).

Example 7

A garlic viscous extract 14.1 g in terms of a dry weight and a liver-hydrolyzed product viscous extract 2.50 g in terms of a dry weight were sufficiently stirred in a suitable amount of purified water, and xylitol 10.0 g were added thereto and dissolved. Then, 10% hydrochloric acid was used to adjust the pH to 4.5, and the whole amount was set to 50 ml with purified water (Sample 7).

Example 8

An epimedium grandiflorum morren viscous extract 84.5 mg in terms of a dry weight, a oriental benzoar tincture 11.9 mg in terms of a dry substance, a Cuscuta chinensis Lam. viscous extract 510 mg in terms of a dry weight, a garlic viscous extract 14.1 g in terms of a dry weight, a ginseng viscous extract 4.67 g in terms of a dry weight and Cornu cervi parvum fluid extract 16.7 mg in terms of a dry weight were sufficiently stirred in a suitable amount of purified water, and xylitol 10.0 g was added thereto and dissolved. Then, 10% hydrochloric acid was used to adjust the pH to 4.5, and the whole amount was set to 50 ml with purified water (Sample 8).

Example 9

In the same manner as in Example 8, 10% hydrochloric acid was used to prepare a test solution of pH 4.0 (Sample 9).

Example 10

In the same manner as in Example 8, 10% hydrochloric acid was used to prepare a test solution of pH 5.0 (Sample 10).

Example 11

In the same manner as in Example 8, sodium hydrogencarbonate was used to prepare a test solution of pH 5.5 (Sample 11).

Example 12

In the same manner as in Example 8, xylitol 5.0 g was added to the whole amount of 50 mL to prepare a test solution (Sample 12).

Example 13

In the same manner as in Example 8, xylitol 15.0 g was added to the whole amount of 50 mL to prepare a test solution (Sample 13).

Example 14

A ginseng viscous extract 4.67 g in terms of a dry weight was sufficiently stirred in a suitable amount of purified water. Then, 10% hydrochloric acid was used to adjust the pH to 5.0, and the whole amount was set to 50 ml with purified water (Sample 14).

Example 15

An epimedium grandiflorum morren viscous extract 3.38 g in terms of a dry extract was sufficiently stirred in a suitable amount of purified water. Then, sodium hydrogencarbonate was used to adjust the pH to 5.0, and the whole amount was set to 50 ml with purified water (Sample 15).

Example 16

A Cuscuta chinensis Lam. viscous extract 3.40 g in terms of a dry weight was sufficiently stirred in a suitable amount of purified water. Then, 10% hydrochloric acid was used to adjust the pH to 4.5, and the whole amount was set to 50 ml with purified water (Sample 16).

Example 17

A garlic viscous extract 14.1 g in terms of a dry weight was sufficiently stirred in a suitable amount of purified water. Then, 10% hydrochloric acid was used to adjust the pH to 5.0, and the whole amount was set to 50 ml with purified water (Sample 17).

Example 18

A liver-hydrolyzed product viscous extract 2.50 g in terms of a dry weight was sufficiently stirred in a suitable amount of purified water. Then, 10% hydrochloric acid was used to adjust the pH to 4.5, and the whole amount was set to 50 ml with purified water (Sample 18).

Example 19

A oriental benzoar tincture 3.17 mg in terms of a dry weight, a civet tincture 4.10 mg in terms of a dry weight, a garlic viscous extract 14.1 g in terms of a dry extract and a ginseng viscous extract 4.67 g in terms of a dry weight were sufficiently stirred in a suitable amount of purified water. Then, 10% hydrochloric acid was used to adjust the pH to 5.0, and the whole amount was set to 50 ml with purified water (Sample 19).

Example 20

A garlic viscous extract 14.1 g in terms of a dry weight and a liver-hydrolyzed product viscous extract 2.50 g in terms of a dry weight were sufficiently stirred in a suitable amount of purified water. Then, 10% hydrochloric acid was used to adjust the pH to 4.5, and the whole amount was set to 50 ml with purified water (Sample 20).

Example 21

An epimedium grandiflorum morren viscous extract 84.5 mg in terms of a dry weight, a oriental benzoar tincture 11.9 mg in terms of a dry weight, a Cuscuta chinensis Lam. viscous extract 10 mg in terms of a dry weight, a garlic viscous extract 14.1 g in terms of a dry weight, a ginseng radix viscous extract 4.67 g in terms of a dry extract and a Cornu Cervi Parvum fluid extract 16.7 mg in terms of a dry weight were sufficiently stirred in a suitable amount of purified water. Then, 10% hydrochloric acid was used to adjust the pH to 4.5, and the whole amount was set to 50 ml with purified water (Sample 21).

Example 22

A panax notoginseng F. H. chen viscous extract 17.2 g in terms of a dry weight was sufficiently stirred in a suitable amount of purified water, and xylitol 6.0 g was added thereto and dissolved. Then, the whole amount was set to 60 ml with purified water to obtain a solution having a pH of 4.9 (Sample 22).

Example 23

A panax notoginseng viscous extract 17.2 g in terms of a dry weight was sufficiently stirred in a suitable amount of purified water, and fructose 6.0 g was added thereto and dissolved. Then, the whole amount was set to 60 ml with purified water to obtain a solution having a pH of 4.9 (Sample 23).

Example 24

A panax notoginseng viscous extract 17.2 g in terms of a dry weight was sufficiently stirred in a suitable amount of purified water, and sucrose 6.0 g was added thereto and dissolved. Then, the whole amount was set to 60 ml with purified water to obtain a solution having a pH of 5.0 (Sample 24).

Example 25

A panax notoginseng viscous extract 17.2 g in terms of a dry weight was sufficiently stirred in a suitable amount of purified water. Then, the whole amount was set to 60 ml with purified water to obtain a solution having a pH of 4.8 (Sample 25).

Test Example 1

Sample 1 and Sample 14 were used to carry out a storage test at 60° C. for 2 weeks. Further, Samples 2 to 8 and Samples 15 to 21 were used to carry out a storage test at 40° C. for 2 weeks. In these cases, the suppressing effect against a precipitate or a suspended matter of the crude drugs with the course of time by adding sugar alcohol was observed. The results thereof are shown in Table 1. As a result thereof, a precipitate or a suspended matter was scarcely observed in storage for 2 weeks in Samples 1 to 8 in which sugar alcohol was added, but in Samples 14 to 21 in which sugar alcohol was not added, a precipitate or a suspended matter was observed with the course of time.

TABLE 1

| | Storage period (week) | | |
|---|---|---|---|
| | 0 | 1 | 2 |
| Sample 1 | - - | - - | - |
| Sample 2 | - - | - | - |
| Sample 3 | - - | - - | - - |
| Sample 4 | - - | - - | - - |
| Sample 5 | - - | - - | - - |
| Sample 6 | - - | - - | - - |
| Sample 7 | - - | - - | - |
| Sample 8 | - - | - - | - - |
| Sample 14 | - - | - - | + |
| Sample 15 | - - | - | + |
| Sample 16 | - - | + | + + |
| Sample 17 | - - | + | + |
| Sample 18 | - - | + | + |
| Sample 19 | - - | - | + |
| Sample 20 | - - | + | + |
| Sample 21 | - - | + | + + |

- -: clear liquid
-: very little precipitation or turbidity was generated
+: precipitation or turbidity was generated
+ +: marked precipitation or turbidity was generated

- -: clear liquid
-: very little precipitation or turbidity was generated
+: precipitation or turbidity was generated
++: marked precipitation or turbidity was generated Test Example 2

Samples 8 to 11 were used to carry out the storage test at 40° C. for 2 weeks. In these cases, an influence exerted on a precipitate or a suspended matter of the crude drugs generated with the course of time due to a change in the pH was observed. The results thereof are shown in Table 2. As a result thereof, precipitate or suspended content was scarcely observed in a range of 4.5 to 5.5, but in the case of a pH 4.0, a precipitate or a suspended matter was observed to be generated with the course of time.

TABLE 2

| | Sample solution pH | Storage period (week) | | |
|---|---|---|---|---|
| | | 0 | 1 | 2 |
| Sample 9 | 4.0 | - - | + + | + + |
| Sample 8 | 4.5 | - - | - - | - - |
| Sample 10 | 5.0 | - - | - - | - - |
| Sample 11 | 5.5 | - - | - - | - - |

- -: clear liquid
-: very little precipitation or turbidity was generated
+: precipitation or turbidity was generated
+ +: marked precipitation or turbidity was generated

- -: clear liquid
-: very little precipitation or turbidity was generated
+: precipitation or turbidity was generated
++: marked precipitation or turbidity was generated Test Example 3

Samples 8, 12, 13 and 21 were used to carry out the storage test at 40° C. for 2 weeks. In these cases, an influence exerted on a precipitate or a suspended matter of the crude drugs generated with the course of time by an adding amount of sugar alcohol was observed. The results thereof are shown in Table 3. As a result thereof, a precipitate or a suspended matter was scarcely observed in Samples 8, 12 and 13.

TABLE 3

|  | Xylitol addition amount (w/v %) | Storage period (week) | | |
| --- | --- | --- | --- | --- |
|  |  | 0 | 1 | 2 |
| Sample 21 | 0.0 | – – | + | + + |
| Sample 12 | 5.0 g (w/v %) | – – | – | – |
| Sample 8 | 10.0 g (w/v %) | – – | – – | – – |
| Sample 13 | 15.0 g (w/v %) | – – | – – | – – |

– –: clear liquid
–: very little precipitation or turbidity was generated
+: precipitation or turbidity was generated
+ +: marked precipitation or turbidity was generated — —: clear liquid
—: very little precipitation or turbidity was generated
+: precipitation or turbidity was generated
++: marked precipitation or turbidity was generated Test Example 4

Samples 22 to 25 were used to carry out the storage test at 40° C. for 2 months. In these cases, an influence exerted on a precipitate or a suspended matter of the crude drugs generated with the course of time by adding saccharides was observed. The results thereof are shown in Table 4. As a result thereof, a precipitate or a suspended matter was scarcely observed in Samples 21, 22, 23 and 24, but in Sample 25 in which saccharides were not added, a precipitate was observed with the course of time.

TABLE 4

|  | Storage period (month) | | | |
| --- | --- | --- | --- | --- |
|  | 0 | 0.5 | 1 | 2 |
| Sample 22 | – – | – – | – – | – – |
| Sample 23 | – – | – – | – – | – – |
| Sample 24 | – – | – – | – – | – – |
| Sample 25 | – – | – – | – | + + |

– –: clear liquid
–: very little precipitation or turbidity was generated
+: precipitation or turbidity was generated
+ +: marked precipitation or turbidity was generated — —: clear liquid
—: very little precipitation or turbidity was generated
+: precipitation or turbidity was generated
++: marked precipitation or turbidity was generated Industrial Applicability According to the present invention, the liquid preparation containing crude drug extracts which is suppressed in generating the precipitate and the suspended content with the course of time can be provided even if crude drug extracts are contained in a high concentration and which is stable over a long period of time.

What is claimed is:

1. A liquid composition that does not contain insoluble matter comprising:
   5 to 50% (w/v) of a garlic extract based on the dry weight of said garlic extract and the total volume of the liquid composition, and, in addition to said garlic extract,
   5 to 40% (w/v) of a saccharide consisting of fructose and/or at least one sugar alcohol based on the weight of the fructose and/or the at least one sugar alcohol and the total volume of the liquid composition;
   wherein said liquid composition has a pH ranging from 4.5 to 5.5; and
   wherein said liquid composition is not fermented.

2. The liquid composition of claim 1, which has been prepared by:
   dissolving a garlic extract in water to provide an aqueous solution,
   centrifuging to remove insoluble matter from the aqueous solution,
   adding fructose and/or at least one sugar alcohol to the centrifuged aqueous solution, and
   adding a pH controller to bring the pH of said centrifuged aqueous solution to 4.5 to 5.5; and, optionally, adding water and refiltering said centrifuged aqueous solution.

3. The liquid composition of claim 1, wherein the saccharide consists of fructose.

4. The liquid composition of claim 1, wherein the saccharide consists of at least one sugar alcohol.

5. The liquid composition of claim 1, wherein the saccharide consists of fructose and at least one sugar alcohol.

6. The liquid composition of claim 1, wherein the garlic extract is obtained from the whole or part of garlic as it exists in nature.

7. The liquid composition of claim 1, wherein the garlic extract is further processed.

8. The liquid composition of claim 1, wherein the garlic extract is a viscous garlic extract.

9. A method for suppressing the formation of a precipitate in a liquid composition comprising:
   adding 5 to 50 w/v% of a monosaccharide and/or at least one sugar alcohol to 5 to 50w/v% of a garlic extract, and
   adjusting the pH to range between 4.5 and 5.5;
   wherein w/v% is based on the dry weight of the garlic extract, the weight of the monosaccharide and/or the at least one sugar alcohol, and the total volume of the liquid composition; and
   wherein said liquid composition is not fermented.

* * * * *